United States Patent [19]

Ohkuma et al.

[11] Patent Number: 5,620,873
[45] Date of Patent: Apr. 15, 1997

[54] PROCESS FOR PREPARING DEXTRIN CONTAINING FOOD FIBER

[75] Inventors: Kazuhiro Ohkuma, Sanda; Yoshio Hanno, Itami; Kazuyuki Inaba, Takarazuka; Isao Matsuda, Itami; Yasuo Katsuda, Kawanishi, all of Japan

[73] Assignee: Matsutani Chemical Industries Co., Ltd., Hyogo-ken, Japan

[21] Appl. No.: 438,113

[22] Filed: May 8, 1995

Related U.S. Application Data

[63] Continuation of Ser. No. 87,091, Jul. 7, 1993, abandoned, which is a continuation of Ser. No. 875,543, Apr. 27, 1992, abandoned, which is a continuation of Ser. No. 379,843, Jul. 14, 1989, abandoned.

[30] Foreign Application Priority Data

| Oct. 7, 1988 | [JP] | Japan | 63-254540 |
| Nov. 25, 1988 | [JP] | Japan | 63-299308 |
| Dec. 5, 1988 | [JP] | Japan | 63-307194 |

[51] Int. Cl.$^6$ ............ C12P 19/22; C12P 19/14; C12N 9/26; C12N 9/34

[52] U.S. Cl. ............... 435/99; 435/96; 435/95; 435/101; 435/103; 435/201; 435/202; 435/203; 435/204; 435/205

[58] Field of Search ............ 426/661, 52; 536/102, 536/103; 435/95, 96, 99, 101, 103, 201, 202, 203, 204, 205

[56] References Cited

U.S. PATENT DOCUMENTS

| 3,663,369 | 5/1972 | Morehouse et al. | 435/99 |
| 3,910,820 | 10/1975 | Holt et al. | 435/94 |
| 3,974,033 | 8/1976 | Harjes et al. | 435/99 |
| 3,992,261 | 11/1976 | Takasaki et al. | 435/210 |
| 4,408,041 | 10/1983 | Hirao et al. | 536/4.1 |
| 4,675,293 | 6/1987 | Gibs | 435/95 |
| 4,855,232 | 8/1989 | Takasaki | 435/193 |
| 4,910,039 | 3/1990 | Fujita et al. | 426/654 |

OTHER PUBLICATIONS

Patent Abstracts of Japan, vol. 11, No. 300 (C–449)[2747], Sep. 29, 1987.

Die Starke, vol. 28, No. 3, Mar. 1976, pp. 77 to 83, Y. Ueno et al, "Studies on pyrodextrinization of corn starch".

Die Starke, vol. 34, No. 5, 1982, pp. 162 to 165, D.B. Wankhede et al, "Preparation and some physiocochemical properties of pyrodextrins of ragi, wheat, jowar and rice starches".

*Primary Examiner*—Michael G. Wityshyn
*Assistant Examiner*—Francisco C. Prats
*Attorney, Agent, or Firm*—Sughrue, Mion, Zinn, Macpeak & Seas

[57] ABSTRACT

A process for preparing a dextrin containing a dietary fiber characterized by dissolving a pyrodextrin in water and causing α-amylase to act on the solution.

17 Claims, No Drawings

PROCESS FOR PREPARING DEXTRIN CONTAINING FOOD FIBER

This is a continuation of application Ser. No. 08/087,091, filed Jul. 7, 1993, now abandoned, which is a continuation application of Ser. No. 07/875,543, filed Apr. 27, 1992, now abandoned, which is a continuation application of Ser. No. 07/379,843, filed Jul. 14, 1989, now abandoned.

The present invention relates to a process for preparing dextrins containing dietary fibers by treating a pyrodextrin with an enzyme.

As is well known, pyrodextrins are prepared by heat-treating a starch at a high temperature. When so treated, the starch molecules undergo hydrolysis and repolymerization to form a complex structure, giving a water-soluble product which contains a considerable proportion of indigestible portion.

In recent years, the dietary life of the Japanese has changed and diversified with a marked reduction in the intake of fibers. The deficiency of fibers is mentioned as one of the causes of diseases of adults. Attention has been directed to the need for dietary fibers, which are called the sixth nutrient following proteins, saccharides, lipids, vitamins and minerals.

The dietary fibers presently available are derived from vegetables and animals, and are soluble or insoluble in water. Polydextrose is also available as a synthetic dietary fiber. These fibers are composed of glucose, derivatives thereof or saccharides, other than glucose, which are bonded together into a fibrous form, or of protein polysaccharides. They have a complex structure, are difficult to digest even when taken into the body, are discharged from the body as they are, and are therefore said to be useful as fibers.

We have conducted research on dietary fibers and conceived the totally novel idea that pyrodextrins, having a marked undesirable odor and undesirable taste and therefore in no way considered useful as dietary fibers, might be usable as food fibers.

The main object of the present invention is to realize the above idea and to provide a process for preparing from a pyrodextrin a dextrin containing a dietary fiber which is satisfactory usable as such.

The object can be fulfilled by a process consisting essentially of dissolving a pyrodextrin in water and causing α-amylase to act on the solution.

Basically, the present invention provides (A) a process for preparing a dextrin by treating pyrodextrin with α-amylase to convert the dextrin to α-limit dextrin and thereby remove the unpleasant odor and undesirable taste from the pyrodextrin. The invention includes the following modes of practicing this basic process.

(B) A process (A) wherein the dextrin treated with α-amylase is thereafter hydrogenated.

(C) A process (A) which comprises causing transglucosidase and/or β-amylase to act on the dextrin treated with α-amylase.

(D) A process (A) which comprises causing glucoamylase to act on the dextrin treated with α-amylase, filtering, deodorizing and desalting the resulting dextrin to obtain a solution of dextrin having a high purity, subjecting the solution to chromatography with use of a strongly acidic cation exchange resin to separate a dextrin fraction, and collecting a dietary fiber from the eluate.

(E) A process (C) wherein the dextrin treated with transglucosidase and/or β-amylase is hydrogenated.

(F) A process (D) wherein transglucosidase is caused to act on the dextrin treated with glucoamylase before the filtration, deodorization and desalting.

(G) A process for preparing a dextrin containing a dietary fiber wherein the dietary fiber-containing dextrin obtained by the process (D) or (F) is further hydrogenated.

(H) A process (A), (B), (C) or (E) wherein the pyrodextrin is one obtained by roasting by a usual method a starch alone or a mixture of a starch and at least one of monosaccharides and oligosaccharides.

The process of the present invention will be described below stepwise.

The pyrodextrin to be used as the starting material can be one heretofore used. To efficiently remove the stimulating odor or undesirable taste of the pyrodextrin therefrom, it is desirable to use in the invention a pyrodextrin which is prepared by adding an aqueous solution of a mineral acid, preferably of hydrochloric acid, to a starch, predrying the mixture to a water content of about 5% and roasting the mixture. The starch can be any of various starches such as potato, corn and cassava starches. Also usable are processed starches commercially available for food uses. An aqueous solution of mineral acid such as sulfuric acid, hydrochloric acid or nitric acid, preferably of hydrochloric acid, having a concentration of about 1 wt. % is uniformly admixed with the starch, preferably by spraying, in an amount of several % by weight. The mixture is predried at about 100° to about 120° C. to a moisture content of about 5%. Subsequently, the mixture is roasted at 150° to 220° C. for about 1 to about 5 hours to obtain a pyrodextrin. The pyrodextrin thus obtained is preferably about 1 to 10 in DE (dextrose equivalent).

In preparing the pyrodextrin, monosaccharides or oligosaccharides can be added to the starch so that the resulting dextrin contains an increased proportion of indigestible dextrin. Usually 50 to 60 wt. % saccharide solution is added in an amount of up to about 10 wt. % based on the starch.

The pyrodextrin is then dissolved in water to a concentration of 30 to 50 wt. % and neutralized to a pH of 5.5 to 6.5, preferably 5.8. Commercial α-amylase (derived from conventional fungi and bacterial source) is added to the solution in an amount of 0.05 to 0.2 wt. % based on the pyrodextrin, and the solution is maintained at a temperature of about 85° to about 100° C. for 30 minutes to 2 hours, permitting the enzyme to act on the dextrin, whereby the dextrin is enzymatically decomposed to α-limit dextrin. The temperature is thereafter elevated to 120° C. to terminate the activity of α-amylase.

The above treatment removes the odor and undesirable taste from the pyrodextrin without greatly increasing the low digestibility thereof, permitting the dextrin to remain sparingly digestible as contemplated.

The resulting liquid is subjected to usual purification steps such as decolorization with active carbon and desalting, concentrated and spray-dried, giving a dextrin powder free from disagreeable odor and taste for use in foods.

According to the invention, the dextrin thus purified can be hydrogenated. When hydrogenated, the dextrin (1) becomes colorless, (2) loses the reducing property due to the removal of reducing group and becomes less amenable to the Maillard reaction, (3) tastes better and feels pleasant on the tongue, and (4) becomes difficult to ferment, for example, free from the attack by lactic acid bacteria. The method of hydrogenation is not limited specifically but can be any known method.

The dextrin is hydrogenated to such an extent that it becomes free from terminal reducing groups. Preferably, the dextrin is hydrogenated, for example, by reconstituting the dextrin to an aqueous solution, adjusting the pH and contacting the solution with hydrogen in the presence of a catalyst such as Raney nickel. For this reaction, the solution may be heated when required.

The present invention further includes a process comprising causing transglucosidase and/or β-amylase to act on the pyrodextrin as treated with α-amylase. The treatment with α-amylase removes the undesired taste and odor from the pyrodextrin as already stated but is likely to give slightly increased digestibility to the dextrin which is preferably completely indigestible. In such a case, at least one of transglucosidase and β-amylase is caused to act on the α-amylase-treated dextrin to permit the dextrin to restore the low degestibility.

For this purpose, the dextrin treated with β-amylase is adjusted in temperature and pH and then treated with transglucosidase in an amount of 0.05 to 0.2 wt. % based on the starting pyrodextrin for 24 to 48 hours. This reaction repolymerizes with large molecules the small molecules of glucose or oligosaccharide which is added as required and further increases the complex structure of pyrodextrin. Upon lapse of the specified period of time, the temperature is temporarily elevated (for example to about 80° C.) to terminate the action of transglucosidase. In place of transglucosidase, amylase is usable, or these two enzymes may be used in combination.

The transglucosidase or β-amylase to be used is a usual one which is commercially available.

The present invention includes a process wherein the dextrin resulting from the treatment with transglucosidase and/or β-amylase is further hydrogenated by the same method as stated above to achieve the same effect as already mentioned.

In the case where transglucosidase is used for treatment, a monosaccharide or oligosccharide can be incorporated in the pyrodextrin as the starting material. The presence of the saccharide results in an increased fiber content. This can be accomplished usually by adding 40 to 60 wt. % solution of such saccharide to the starch to be roasted into the pyrodextrin, in an amount of about 1 to about 10 wt. % based on the starch, and roasting the mixture. Examples of useful monosaccharides are those already known as such. Also usable are known oligosaccharides.

The present invention further includes a process for preparing a dextrin having a high dietary fiber content by causing glucoamylase to act on the dextrin treated with α-amylase, subjecting the resulting dextrin to a usual purification step to obtain a solution of dextrin having a high purity, subjecting the solution to chromatography with use of a strongly acidic cation exchange resin to separate a dextrin fraction, and collecting a dietary fiber from the eluate. This process will be described below.

Glucoamylase is caused to act on the dextrin as treated with α-amylase by adjusting the liquid resulting from the treatment with α-amylase to a temperature of up to 100° C. and to an acid pH value, adding glucoamylase to the liquid in an amount of 0.05 to 0.2 wt. % based on the starting pyrodextrin and maintaining the liquid at a temperature of about 55° C. for 24 to 48 hours. The small molecules as of oligosaccharide present in the liquid are decomposed to glucose by this reaction. Upon lapse of the specified period of time, the temperature is elevated, for example, to about 80° C. to terminate the enzymatic action of glucoamylase. The glucoamylase to be used is a usual one commercially available.

The above treatment affords a mixture of the dietary fiber originally contained in the pyrodextrin and a low-molecular-weight component corresponding to readily digestible glucose.

When required, transglucosidase can be caused to act on the mixture resulting from the treatment with glucoamylase, whereby the readily digestible glucose converted by the glucoamylase is repolymerized and made indigestible to substantially increase the proportion of the indigestible component. However, the transglucosidase acts to polymerize glucose to produce a indigestible portion, so that the resulting product is a mixture of the food fiber originally contained in the pyrodextrin and the portion thus polymerized and made indigestible.

In the above process, a monosaccharide or oligosaccharide can be added to the starting starch to give an increased content of indigestible dextrin. For this purpose, 40 to 60 wt. % solution of such saccharide is added in an amount of up to about 10 wt. % based on the starch. The treatment with transglucosidase is conducted using this enzyme in an amount of about 0.05 to about 0.2 wt. % based on the pyrodextrin and maintaining the mixture at 50° to 65° C., preferably 52° to 57° C., for 24 to 48 hours.

The liquid resulting from the above procedure is subjected to usual purification steps such as decolorization with activated carbon and desalting through ion exchange, concentrated to about 50 wt. % solution and thereafter passed through a column of strongly acidic cation exchange resin for chromatography to separate a high-molecular-weight fraction (indigestible dextrin) from a glucose fraction. The high-molecular-weight fraction is collected, concentrated and dried to obtain a indigestible dextrin having a high dietary fiber content.

Examples of useful strongly acidic cation exchange resins are those generally available commercially. More specific examples of preferred resins are AMBERLITE IR-116, AMBERLITE IR-118, AMBERLITE IR-120B, XT-1022E, XT-471F (all products of Japan Organo Co., Ltd.), DIAION SK-1B, DIAION SK102, DIAION SK104, DIAION SK106, DIAION SK110, DIAION SK112, DIAION SK116, DIAION FR01 (all products of Mitsubishi Chemical Industries, Ltd.), XFS-43281.00, XFS-43280.00, XFS-43279.00 and XFS-43278.00 (all products of Dow Chemical Co.).

Before the resin is used for chromatography, it is desirable to use the resin as an alkali metal type or alkaline earth metal type. To separate the high-molecular-weight dextrin from glucose efficiently, it is desirable to pass the liquid through the column at a flow rate adjusted to the resin used. The flow rate is preferably in the range of SV=0.1 to 0.6. If the flow rate is outside this range, inefficient separation tends to result. The temperature of the liquid to be passed through the column is preferably 20° to 70° C. Lower temperatures entail inefficient separation and give an increased viscosity to the liquid to produce an adverse effect on the resin, whereas higher temperatures will color the liquid brown and otherwise degrade the liquid.

The indigestible dextrin thus prepared contains 80 to 95% of dietary fiber calculated as solids and determined by the Prosky-AOAC method or Southgate method.

According to the invention, the dextrin obtained by the column chromatography can be further hydrogenated. The hydrogenation produces the effect already described.

The dextrin obtained by the process of the invention is usable as admixed with a wide variety of foods such as beverages, ice cream, bread, dressing, candies and processed marine products.

The present invention will be described in greater detail with reference to the following examples.

EXAMPLE 1

Commercial potato starch (5,000 kg) was placed into a ribbon mixer, 150 liters of 1.0% hydrochloric acid was sprayed onto the starch with stirring, and then uniformly mixed therewith by a crusher, and the mixture was aged in the ribbon mixer for 5 hours. The mixture was predried to a moisture content of 3% by a flash dryer, then continuously charged into a rotary kiln roaster and roasted at 180° C. for 2 hours.

Water (4,000 liters) was added to 2,000 kg of the pyrodextrin obtained by the above method, the mixture was adjusted to a pH of 6.0, and the dextrin was hydrolyzed at 95° C. for 1 hour with 0.2% of α-amylase (TERMAMYL 60L, product of Novo Industri A/S) added thereto. The reaction mixture was purified by decolorization and desalting and dried by a spray dryer, giving 1,700 kg of purified dextrin. The dextrin had a dietary fiber content of 35% as determined by the Prosky-AOAC method.

EXAMPLE 2

The fiber-containing dextrin prepared in Example 1 was made into a 40% solution, to which 8% secondary sodium phosphate solution was added in an amount of 0.4% based on the solution. The solution was adjusted to a pH of 9.5 with 20% sodium hydroxide solution and then placed into an autoclave. Raney nickel (R-100, product of Nikko Rika Co., Ltd.) was added to the solution in an amount of 1% based thereon, hydrogen gas was introduced into the autoclave to a gauge pressure of 95 kg/cm$^2$ at a temperature of 21° C., and the mixture was heated at 130° C. for 120 minutes while shaking the autoclave to effect a reduction reaction. The reaction mixture was allowed to cool, active carbon was added thereto, and the mixture was filtered. The filtrate was desalted with ion exchange resin and concentrated to obtain a 75% solution.

The concentrate was in the form of a colorless transparent consistent solution having a dietary fiber content of 27% (as determined by the Prosky-AOAC method).

EXAMPLE 3

Preparation of dietary fiber-containing foods

Foods were prepared according to the following formulations with addition of the dietary fiber-containing dextrin obtained in Example 1. The foods had the fiber contents given below.

| bread | |
|---|---|
| Flour | 250 g |
| Sugar | 17 g |
| Common salt | 5 g |
| Expressed yeast | 3 g |
| Yeast food | 6 g |
| Butter | 11 g |
| Dextrin obtained in Example 1 | 30 g |
| Water | 190 g |
| The above ingredients were made into bread by the usual method. | |
| Dietary fiber content | 3.7% |
| Ice cream | |
| Butter | 6.5 g |
| Condensed milk | 8.0 g |
| Skim milk powder | 6.5 g |
| Dextrin obtained in Example 1 | 8.0 g |
| Sugar | 5.0 g |
| Emulsifier | 0.3 g |
| Stabilizer | 0.2 g |
| Water | 65.5 g |
| The above ingredients were made into ice cream by the usual method. | |
| Dietary fiber Content | 2.8% |

| Carbonated drink (soda pop) | |
|---|---|
| Sucrose | 125 g |
| Citric acid | 1.5 g |
| Sodium citrate | 0.1 g |
| Vitamin C | 0.15 g |
| Essence | 1.0 ml |
| Dextrin obtained in Example 1 | 50 g |
| Carbonated water | 520 g |
| Water | 385 ml |
| A carbonated drink was prepared from the above ingredients by the usual method. | |
| Dietary fiber content | 1.8% |
| Dressing | |
| Salad oil | 56 g |
| Vinegar | 30 g |
| Spice | 3.5 g |
| MSG | 0.5 g |
| Dextrin obtained in Example 1 | 10 g |
| A dressing was prepared from the above ingredients by the usual method. | |
| Dietary fiber content | 3.5% |

Foods were prepared, each by the usual method, according to the following formulations with addition of the dietary fiber-containing dextrin obtained in Example 2. The foods had the dietary fiber contents given below.

| Candy | |
|---|---|
| Sucrose | 50 g |
| Starch syrup | 35 g |
| Tartaric acid | 0.15 g |
| Citric acid | 0.35 g |
| Food pigment | suitable amount |
| Food flavor | suitable amount |
| Dextrin obtained in Example 2 | 20 g |
| Dietary fiber content | 7.0% |
| Boiled fish paste (kamaboko) | |
| Ground fish meat (surimi) | 100 parts |
| Common salt | 3 parts |
| Starch | 5 parts |
| Dextrin obtained in Example 2 | 7.5 parts |
| Water | 32.5 parts |
| Dietary fiber content | 3.0% |

Comparative Example 1

Maltodextrin (PINE DEX #1, product of Matsutani Chem. Ind. Co., Ltd.) equivalent in DE value to the pyrodextrin obtained in Example 1 was concentrated to 50%, and 0.2% of transglucosidase was added to the concentrate to effect reaction for 48 hours, whereby the following sucrose was obtained.

DP1 65%, DP2 10.5% (maltose 2.3%, kojibiose 2.5%, isomaltose 5.7%), DP3 6.2% (maltotriose 1.2%, panose 3.8%, isomaltotriose 1.2%), and DP4 up 18.3%, indigestible dextrin content 5.0%.

EXAMPLE 4

A 5 ml quantity of 1.0% hydrochloric acid solution was sprayed on 100 g of commercial potato starch using compressed air. The starch was then uniformly stirred in a mixer, placed into an aluminum vat, predried in a dryer at 110° C. for 1 hour and thereafter roasted at 150° C. for 3 hours. The pyrodextrin obtained was 6.8 in DE, 160 cps in viscosity (concentration 50%, 30° C.) and 57% in indigestible dextrin content.

The pyrodextrin (100 g) prepared as above was dissolved in 100 g of hot water, the solution was adjusted to a pH of 5.8 with 1N sodium hydroxide, and 0.1% of α-amylase TERMAMYL 120L, product of Novo Industrie A/S was added to the solution to effect reaction at 95° C. One hour later, the reaction mixture was heated to 115° C. to complete the reaction. The reaction mixture was then adjusted to a pH of 5.5 and a temperature of 55° C., and 0.05% of β-amylase (product of Amano Pharmaceutical Co., Ltd.) and 0.1% of transglucosidase (product of the same) were added to the mixture, followed by reaction for 24 hours to give a dextrin having the following composition.

DP1 15.8%, DP2 10.7% (maltose 0.6%, kojibiose 0.3%, isomaltose 9.8%), DP3 5.3%, DP4 and up 68.2%, viscosity 75 cps (concentration 50%, 30° C.), indigestible dextrin content 72%.

EXAMPLE 5

A 4 ml quantity of 1.2% hydrochloric acid and 15 g of 50% aqueous glucose solution were sprayed on 100 g of tapioca starch using compressed air. The starch was then predried under the same condition as in Example 4 and thereafter roasted at 170° C. for 2 hours. The pyrodextrin obtained was 2.0 in. DE, 250 cps in viscosity (50%, 30° C.) and 45% in indigestible dextrin content.

The pyrodextrin (100 g) obtained as above was dissolved in 200 c.c. of hot water, the solution was neutralized with calcium carbonate powder, and 0.2% of α-amylase (BIOZYME C, product of Amano Pharmaceutical Co., Ltd.) was added to the solution to effect reaction at 60° C. Three hours thereafter, the reaction mixture was heated to 85° C. to complete the reaction. The reaction mixture was then concentrated to 55%, and 0.1% of transglucosidase (product of Amano Pharmaceutical Co., Ltd.) was added to the concentrate to effect reaction for 48 hours, giving a dextrin of the following composition.

DP1 22.5%, DP2 9.4% (maltose 1.3%, kojibiose 0.7%, isomaltose 7.4%), DP3 3.9% (maltotriose 0.3%, panose 1.7%, isomaltotriose 1.9%), DP4 and up 64.2%.

Viscosity 53.5 cps (concentration 50%, 30° C.), indigestible dextrin content 65%.

Reference Example 1

Tapioca starch (10,000 kg) was suspended in 12,000 liters of water containing 1,500 kg of sodium sulfate, 3,000 liters of 3% aqueous solution of sodium hydroxide was added dropwise to the suspension, and 800 liters of propylene oxide was added to the mixture, followed by reaction at 43° C. for 20 hours. The reaction mixture was neutralized with sulfuric acid, washed with water, dewatered by centrifuging and dried by a flash dryer to obtain hydroxypropyl starch, which was 12.5% in moisture content and 0.145 in DS.

EXAMPLE 6

The hydroxypropyl starch (5,000 kg) obtained in Reference Example 1 was placed into a ribbon mixer, 200 liters of 1.2% hydrochloric acid and 500 kg of commercial maltose syrup (MC-75, product of Nihon Shokuhin Kako Co., Ltd.) adjusted to a concentration of 50% were sprayed on the starch with stirring using compressed air, and the mixture was stirred for 1 hour, homogenized with a crusher and therafter aged in the ribbon mixer for 12 hours. The mixture was predried to a moisture content of 3.5% by a flash dryer, then continuously charged into a rotary kiln roaster, and retained in the roaster at 175° C. for 1.5 hours for roasting. The pyrodextrin obtained was 9.0 in DE, 200 cps in viscosity (50%, 30° C.) and 45% in indigestible dextrin content.

The pyrodextrin (2,000 kg) prepared by the above method was dissolved in 4,000 liters of hot water, the solution was adjusted to a pH of 6.0 with 20% sodium hydroxide, and 0.3% of α-amylase. (TERMAMYL 60L, product of Novo Industri A/S) was added to the solution, followed by reaction at 95° C. One hour thereafter, the reaction mixture was heated to 115° C. to complete the reaction. The mixture was adjusted to a concentration of 55%, and 0.2% of S-amylase (product of Amano Pharmaceutical Co., Ltd.) and 0.1% of transglucosidase (product of the same) were added to the mixture, followed by reaction for 48 hours to give a dextrin having the following composition.

DP1 7.4%, DP2 8.7% (maltose 1.1%, kojibiose 0.6%, isomaltose 7.0%), DP3 6.3% (maltotriose 0.7%, panose 2.7%, isomaltotriose 2.9%), DP4 and up 77.6%, viscosity 70 cps (50%, 30° C.), indigestible dextrin content 60%.

EXAMPLE 7

Commercial potato starch (5,000 kg) was placed into a ribbon mixer, 200 liters of 1.0% hydrochloric acid was sprayed onto the starch with stirring and then uniformly mixed therewith by a crusher, and the mixture was aged in the ribbon mixer for 10 hours. The mixture was predried to a moisture content of 3% by a flash dryer, then continuously charged into a rotary kiln roaster and roasted at 185° C. for 2 hours. The pyrodextrin obtained was 7.8 in DE, 120 cps in viscosity (50%, 30° C.) and 56% in indigestible dextrin content.

Hot water (4,000 liters) was added to 2,000 kg of the pyrodextrin obtained by the above method, the solution was adjusted to a pH of 6.0 with 20% sodium hydroxide, and the dextrin was hydrolyzed at 95° C. for 1 hour with 0.2% of α-amylase (TERMAMYL 60L, product of Novo Industri A/S) added thereto. The reaction mixture was concentrated to 50%, 0.2% transglucosidase was added to the concentrate to effect reaction for 48 hours, and the reaction mixture was purified by decolorization, desalting, etc. to give a dextrin having the following composition.

DP1 10.6%, DP2 9.4% (maltose 0.3%, kojibiose 0.7%, isomaltose 7.7%), DP3 5.2% (maltotriose 0.6%, panose 2.0%, isomaltotriose 2.6%), DP4 and up 74.8%.

Viscosity 55 cps (50%, 30° C.), indigestible dextrin content 67%.

EXAMPLE 8

A carbonated drink of the following formulation was prepared using the indigestible dextrin obtained in Example 7, and was subjected to a sensory test and checked for the effect of the dietary fiber contained therein. The drink tasted good and found effective for remedying constipation.

| | |
|---|---|
| Dextrin obtained in Example 7 | 50 g |
| Granulated sugar | 125 g |
| Citric acid | 1.5 g |
| Sodium citrate | 0.1 g |
| Vitamin C | 0.15 g |
| Carbonated water | 520 g |
| Water | 385 g |

Test for constipation remedy effect

The drink was given to 10 persons (5 males and 5 females) with constipation in an amount of 200 c.c./day for testing. Two days later, 8 persons resumed normal bowel movements.

TABLE 1

|  | Day 1 | Day 2 | Day 3 | Day 4 | Day 5 |
| --- | --- | --- | --- | --- | --- |
| Constipation | 2 | 1 | 2 | 0 | 1 |
| Hard feces | 2 | 1 | 0 | 2 | 2 |
| Normal | 5 | 7 | 6 | 7 | 6 |
| Soft feces | 1 | 1 | 1 | 1 | 1 |
| Diarrhea | 0 | 0 | 1 | 0 | 0 |

Comparative Example 2

Maltodextrin (PINE DEX #1, product of Matsutani Chem. Ind. Co., Ltd.) equivalent in DE value to the pyrodextrin obtained in Example 7 was concentrated to 50%, and 0.2% of transglucosidase was added to the concentrate to effect reaction for 48 hours, whereby a saccharide was obtained with the following composition.

DP1 65%, DP2 10.5% (maltose 2.3%, kojibiose 2.5%, isomaltose 5.7%), DP3 6.2% (maltotriose 1.2%, panose 3.8%, isomaltotriose 1.2%), DP4 and up 18.3%, indigestible dextrin content 5.0%.

In Reference Example 1, Example 4 to 8 and Comparative Example 2, the indigestible dextrin content was determined by the following method.

Method of Determining Dextrin Content

One gram of sample was accurately weighed out, 50 ml of water was added thereto, the solution was adjusted to a pH of 5.8, and 0.1 ml of α-amylase (TERMAMYL 120L, product of Novo Industri A/S) was added to the solution, followed by reaction at 95° C. for 30 minutes. The reaction mixture was cooled, then adjusted to a pH of 4.5 and reacted with 0.1 ml of amyloglucosidase (product of Sigma) at 60° C. for 30 minutes. The reaction mixture was thereafter heated to 90° C. to complete the reaction. The reaction mixture was filtered, and the filtrate was concentrated to 5% and subjected to HPLC. The amount of glucose was determined from the composition of the sugar fraction. The indigestible dextrin content was given by the following equation.

*Indigestible dextrin content (%)*

$=100-glucose\ produced\ (\%)$

EXAMPLE 9

A 10 kg quantity of a pyrodextrin (ARABIX #7, product of Matsutani Chem. Ind. Co., Ltd.) was dissolved in 20 kg of water, the solution was adjusted to a pH of 5.5, and 0.2 wt. % of α-amylase (KLEISTASE KD, product of Daiwa Kasei K.K.) was added to the solution to effect reaction at 85° C. for 1 hour, and the reaction mixture was then heated at 120° C. for 15 minutes to terminate the action of amylase. The reaction mixture was cooled to 55° C., then adjusted to a pH of 4.5 and reacted with 0.1 wt. % of glucoamylase (product of Daiwa Kasei K.K.) added thereto for 36 hours for saccharification, whereupon the reaction mixture was adjusted to a pH of 3.5 to terminate the action of glucoamylase. The mixture was then purified with active carbon and ion exchange resin and thereafter concentrated to give 1.5 kg of 50% solution. The solution had the saccharide composition of 51.2% glucose, 2.2% disaccharide, 3.9% trisaccharide and 42.8% tetra- to poly-saccharides. A 100-ml portion of the solution was passed at SV=0.25 through a column packed with 5 liters of XFS-43279.00 (product of Dow Chemical Co.) which is an alkali metal type strongly acidic cation exchange resin. Subsequently, water was passed through the column to collect a high-molecular-weight dextrin. The dextrin had the composition of 4.4% glucose, 1.2% monosaccharide, 1.7% trisaccharide and 92.1% tetra- to poly-saccharides, and a dietary fiber content of 83.9% as determined by the Prosky-ACAC method.

EXAMPLE 10

Four liters of water was added to 2 kg of a pyrodextrin (Avedex 36LAC, product of Avebe), the solution was adjusted to a pH of 6.0, and 4 g of alpha-amylase (TERMAMYL 60L, product of Novo Industri A/S) was added to the solution to effect reaction at 95° C. for 1 hour. The reaction mixture was maintained at 140° C. for 15 minutes to terminate the enzymatic activity. The mixture was thereafter treated in the same manner as in Example 1 to obtain 1800 g of liquid product (concentration 50%) having a high indigestible dextrin.

The solution (1.0 kg) was adjusted to a pH of 9.5 with addition of 2 ml of 8% solution of secondary sodium phosphate and 2% solution of sodium hydroxide. The solution was placed into an autoclave, 0.1 kg of Raney nickel was added to the solution, hydrogen gas to introduced into the autoclave to a pressure of 93 kg/cm$^2$ at 25° C., and the mixture was thereafter heated at 130° C. to effect reaction for 90 minutes. The reaction mixture was allowed to cool, and then filtered with addition of active carbon. The filtrate was desalted with an ion exchange resin and concentrated to give 0.7 kg of 70% solution. The solution was colorless, transparent and consistent and had a dietary fiber content of 82% (as determined by the Prosky-AOAC method).

The product before the fractionation with the ion exchange resin (referred to as "A" below) was compared with the product as fractionated with the resin (referred to as "B" below) in properties. Table 2 shows the result.

TABLE 2

|  | Sweetness* | Viscosity** (cps) | Average molecular weight | DE | Hygroscopicity (%) |
| --- | --- | --- | --- | --- | --- |
| A | 10 | 8.2 | About 1500 | 10 | 16 |
| B | 5 | 7.0 | About 2000 | 4.6 | 15 |

*Relative to sucrose which is taken as 100.
**30%, 30° C.

As to the hygroscopicity, the product remained free of deliquescence regardless of the fractionation when allowed to stand at 25° C. at 81% RH for 100 hours.

What is claimed is:

1. A process for preparing a dextrin containing at least 27% dietary fiber as measured by the Prosky-AOAC method or at least 45% dietary fiber as measured by HPLC method, said process comprising dissolving a pyrodextrin in water and causing α-amylase to act on the solution, said pyrodextrin having a dextrose equivalent of 1 to 10, and prepared by the steps of adding at least 300 ppm of HCl to a starch, heating at 100° to 120° C. until the water content is about 5%, followed by roasting at 150° to 220° C. for 1 to 5 hours.

2. A process according to claim 1 further comprising hydrogenation of the dextrin.

3. A process according to claim 1 further comprising treatment of the dextrin with at least one enzyme selected from the group consisting of transglucosidase and β-amylase.

4. A process according to claim 3 further comprising hydrogenation of the dextrin treated with said at least one enzyme.

5. A process according to claim 1 further comprising treatment of the dextrin with glucoamylase, filtering, deodorizing and desalting the resultant product, chromatographing on a strongly acidic cation exchange resin and collecting a dietary fiber from the eluate.

6. A process according to claim 5 further comprising treatment of the dextrin with transglucosidase.

7. A process according to claim 5 or 6 further comprising hydrogenation.

8. The process of claim 1, wherein the pyrodextrin has a dextrose equivalent of 6.8 to 10.

9. A dietary fiber-containing dextrin which contains at least 27% dietary fiber as measured by the Prosky-AOAC method or at least 45% indigestible components as measured by HPLC method and which is prepared by a process comprising the steps of dissolving a pyrodextrin in water and hydrolyzing the pyrodextrin with alpha-amylase to obtain the dietary fiber-containing dextrin, said pyrodextrin having a dextrose equivalent of 1 to 10, and prepared by the steps of adding at least 300 ppm of HCl to a starch, drying the mixture at 100° to 120° C. until the water content of the starch is about 5% and roasting the dried starch at 150° to 220° C. for 1 to 5 hours.

10. The dextrin of claim 9 wherein the process further comprises the step of hydrogenation of the hydrolyzed pyrodextrin.

11. The dextrin of claim 9 wherein the process further comprises the step of treatment of the hydrolyzed pyrodextrin with beta-amylase.

12. The dextrin of claim 9 wherein the process further comprises the step of treatment of the hydrolyzed pyrodextrin with transglucosidase.

13. The dextrin of claim 9 wherein the process further comprises the step of treatment of the hydrolyzed pyrodextrin with beta-amylase and transglucosidase.

14. The dextrin of claim 9 wherein the pyrodextrin is dissolved in water in a concentration of 30 to 40% by weight.

15. The dextrin of claim 9 wherein alpha-amylase is used in an amount of 0.05 to 0.2% by weight based on the weight of the pyrodextrin.

16. The dextrin of claim 9 wherein alpha-amylase is acted on the pyrodextrin at 85° to 100° C. for 30 to 120 minutes.

17. The dextrin of claim 9, wherein the pyrodextrin has a dextrose equivalent of 6.8 to 10.

\* \* \* \* \*

UNITED STATES PATENT AND TRADEMARK OFFICE
CERTIFICATE OF CORRECTION

PATENT NO.   : 5,620,873
DATED        : April 15, 1997
INVENTOR(S)  : Kazuhiro Ohkuma et al It is certified that error appears in the above-identified patent and that said Letters Patent is hereby corrected as shown below:

On title page, item

[75] Inventors: delete "Kazuyuki Inaba" and insert --Kazuyuki Inada--.

Signed and Sealed this

Twelfth Day of August, 1997

*Attest:*

BRUCE LEHMAN

*Attesting Officer*   *Commissioner of Patents and Trademarks*